United States Patent
Ohtsuka

(10) Patent No.: US 7,252,182 B2
(45) Date of Patent: Aug. 7, 2007

(54) VIBRATION ISOLATION STRUCTURE FOR IMAGE FORMING APPARATUS

(75) Inventor: Yuzuru Ohtsuka, Minami-ashigara (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 11/055,517

(22) Filed: Feb. 11, 2005

(65) Prior Publication Data

US 2005/0178629 A1   Aug. 18, 2005

(30) Foreign Application Priority Data

Feb. 16, 2004   (JP)   ............................. 2004-038901

(51) Int. Cl.
  *F16F 7/10*   (2006.01)
  *A61B 6/00*   (2006.01)
  *H05G 1/10*   (2006.01)

(52) U.S. Cl. ........................ 188/378; 378/102; 250/582

(58) Field of Classification Search ........ 188/378–380; 267/136; 248/550–638; 250/370.09; 355/53, 355/76

See application file for complete search history.

(56) References Cited

U.S. PATENT DOCUMENTS

| | | | |
|---|---|---|---|
| 5,418,609 A * | 5/1995 | Dunne ........................ 356/5.01 |
| 5,601,274 A * | 2/1997 | Minor et al. ................. 248/594 |
| 6,226,075 B1 * | 5/2001 | Loopstra et al. .............. 355/76 |
| 6,481,887 B1 | 11/2002 | Mirabella | |
| 6,493,062 B2 * | 12/2002 | Tokuda et al. ................ 355/53 |
| 6,512,571 B2 * | 1/2003 | Hara ........................... 355/53 |
| 6,626,412 B1 * | 9/2003 | Lindsay ...................... 248/550 |
| 2002/0014594 A1 * | 2/2002 | Endo ..................... 250/370.09 |

FOREIGN PATENT DOCUMENTS

| | | |
|---|---|---|
| JP | 10-246999 A | 9/1998 |
| JP | 2001-299743 A | 10/2001 |
| JP | 2002-255279 A | 9/2002 |

* cited by examiner

Primary Examiner—Christopher P. Schwartz
(74) Attorney, Agent, or Firm—Sughrue Mion, PLLC

(57) ABSTRACT

A vibration isolation structure for an image-forming apparatus includes an exposure unit disposed in a vehicle compartment, for applying radiation to a subject and capturing a radiation image of the subject; a support post fixedly mounted in the compartment of the vehicle; a holder for holding the exposure unit; and a vibration-suppressing mechanism for connecting the support post and the holder to each other to suppress vibrations transmitted from the vehicle through the support post to the holder. The vibration-suppressing mechanism may include a resilient member disposed between the support post and the holder, holding the holder swingably with respect to the support post. The resilient member may include a helical spring or a plurality of resilient components. The resilient member may have characteristics established depending on the weight and position of the center of gravity of the holder or exposure unit, or conditions in which the vehicle is driven.

6 Claims, 12 Drawing Sheets

VIBRATION ISOLATION STRUCTURE FOR IMAGE FORMING APPARATUS

BACKGROUND OF THE INVENTION

1. Field of the Invention:

The present invention relates to an image forming apparatus for being mounted on a vehicle, and more particularly to a vibration isolation structure for preventing vibrations from being transmitted from a vehicle to an exposure unit of an image forming apparatus that is mounted on the vehicle.

2. Description of the Related Art:

There have heretofore been known image forming apparatus for recording radiation image information of a subject such as a human body on a stimulable phosphor sheet having a stimulable phosphor layer. A stimulable phosphor is a phosphor which, when exposed to an applied radiation (X-rays, α-rays, β-rays, γ-rays, electron beams, ultraviolet radiation, or the like), stores part of the energy of the radiation, and, when subsequently exposed to applied stimulating rays such as visible light, emits photostimulated luminescence in proportion to the stored energy of the radiation.

An image forming apparatus disclosed in Japanese Laid-Open Patent Publication No. 2001-299743 is installed on a vehicle such as a mobile medical examination car and mounted on the chassis of the mobile medical examination car. The disclosed image forming apparatus can take pictures of subjects for medical examination within the vehicle and at remote sites.

Generally, image forming apparatus for use on vehicles have optical systems that are subject to vibrations. For example, Japanese Laid-Open Patent Publication No. 2001-299743 discloses an image forming apparatus comprising a medical image scanner for scanning patient's bodies. When the image forming apparatus is installed on a vehicle, the optical system thereof is subject to vibrations from the wheels of the vehicle while the vehicle is being driven or vibrations from the engine or electric generator on the vehicle, and may tend to decrease in function.

Heretofore, the image forming apparatus for use on vehicles have not been equipped with a vibration suppressing mechanism for blocking vibrations from being applied from the vehicle to the optical system. Consequently, since the optical system decreases more in function as the resolution of the image forming unit of the image forming apparatus for reading images is higher, it has been difficult to install highly accurate image forming apparatus on vehicles.

Japanese Laid-Open Patent Publication No. 2002-255279 discloses a vibration isolation means for isolating vibrations that are produced on a workpiece that is conveyed. The disclosed vibration isolation means is disposed between a base plate for holding a box such as a container or the like carried by an aircraft or the like and the floor of the aircraft, and isolates vibrations against transmission to the box. When the floor is vibrated, the vibration isolation means suppresses vibrations transmitted from the floor to the base, thereby preventing vibrations from being transmitted to the box.

There have not been available in the art image forming apparatus for use on vehicles which have vibration isolation means for preventing vibrations generated when the vehicles are driven from being transmitted to the image forming apparatus. There has been a demand for carrying a high-precision image forming apparatus which is susceptible to vibrations on a vehicle such as a mobile medical examination car or the like and capturing images of subjects such as patients or the like at remote locations with the image forming apparatus.

In order to prevent vibrations from occurring in an image forming apparatus carried on a vehicle, it may be proposed to install an image forming apparatus, rather than a box such as a container or the like, on the base plate disclosed Japanese Laid-Open Patent Publication No. 2002-255279, and place the base plate on the floor of the vehicle. With this proposed arrangement, it may be possible to prevent vibrations from being transmitted to the image forming apparatus with the vibration isolation means disposed between the base plate and the floor.

However, the disclosed vibration isolation means for preventing vibrations from being transmitted is large in size as it is designed for use on an aircraft. It is difficult to apply the disclosed vibration isolation means to image forming apparatus for use on a vehicle such as mobile medical examination car or the like, and the disclosed vibration isolation means itself is highly costly to manufacture.

SUMMARY OF THE INVENTION

It is a general object of the present invention to provide a vibration isolation structure for an image forming apparatus mounted on a vehicle, the vibration isolation structure being capable of preventing vibrations from being transmitted from the vehicle to an exposure unit of the image forming apparatus.

According to the present invention, a holder holding an exposure unit of an image forming apparatus is joined to a support post fixedly mounted in a compartment of a vehicle by a vibration suppressing mechanism for suppressing vibrations from the vehicle. When the vehicle carrying the image forming apparatus is driven, vibrations generated by the vehicle are transmitted through the support post to the vibration suppressing mechanism. The vibrations are dampened by the vibration suppressing mechanism before being transmitted to the holder. Therefore, the vibrations from the vehicle are suppressed, and hence the exposure unit mounted on the holder for capturing radiation image information is effectively protected from the vibrations.

The vibration suppressing mechanism comprises a resilient member disposed between the support post and the holder and holding the holder swingably with respect to the support post. Thus, the vibration suppressing mechanism disposed between the support post and the holder does not make the image forming apparatus significantly large in size, and allows a limited space in the compartment of the vehicle to be utilized effectively by the image forming apparatus.

The vibration suppressing mechanism in the form of a resilient member makes it possible to dampen vibrations from the vehicle based on the resiliency of the resilient member. If conditions with respect to the vibrations generated by the vehicle and/or the weight, etc. of the holder held by the vibration suppressing mechanism is changed, then the characteristics (e.g., material characteristics) of the resilient member are changed to allow the vibration suppressing mechanism to appropriately dampen vibrations transmitted from the vehicle.

The above and other objects, features, and advantages of the present invention will become more apparent from the following description when taken in conjunction with the accompanying drawings in which preferred embodiments of the present invention are shown by way of illustrative example.

DETAILED DESCRIPTION OF THE EXEMPLARY EMBODIMENTS

Figure 1:
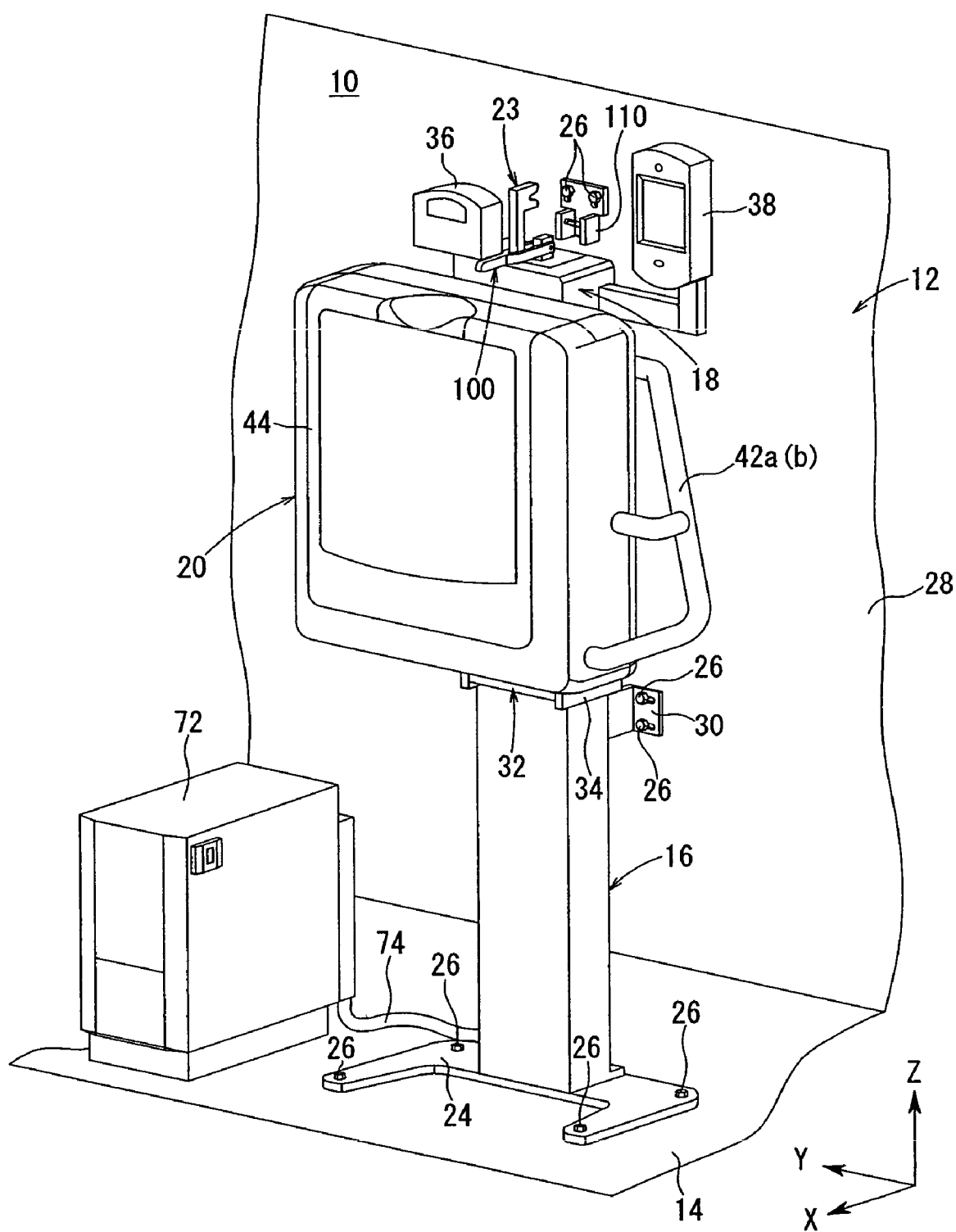
FIG. 1 is a front perspective view showing an image forming apparatus incorporating a vibration isolation mechanism according to an embodiment of the present invention, which is installed in a compartment of a vehicle.

FIG. 1 shows in fragmentary perspective an image forming apparatus 10 incorporating a fixing structure according to an embodiment of the present invention, which is installed in a compartment of a vehicle.

Figure 2:
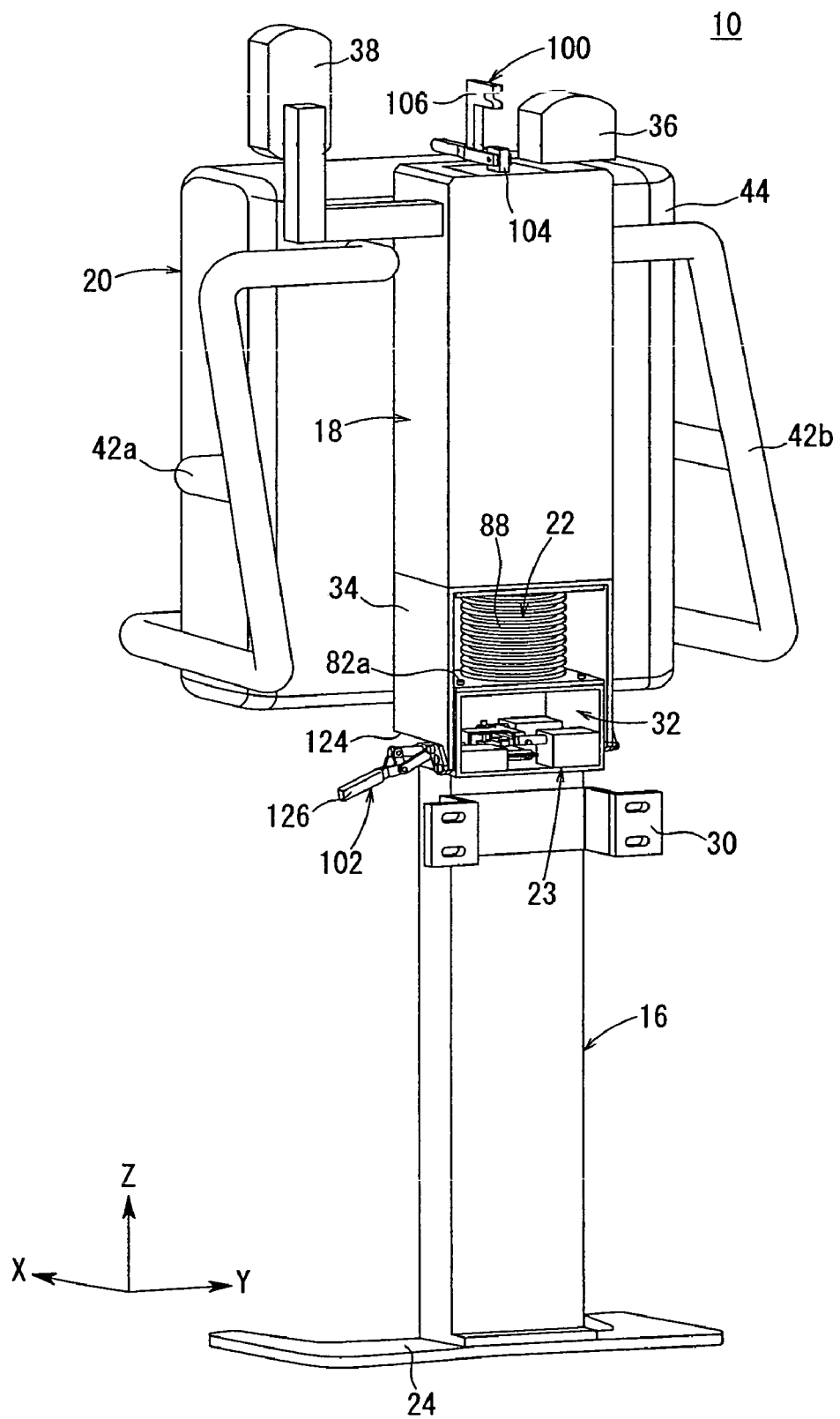
FIG. 2 is a rear perspective view of the image forming apparatus shown in FIG. 1, as viewed from a wall surface of the vehicle.

As shown in FIGS. 1 and 2, the image forming apparatus 10 has a first support post (support post) 16 erected on a floor 14 of a vehicle 12 (see FIG. 12), a second support post 18 (see FIG. 2) formed separately from and mounted on an upper end of the first support post 16, a main unit (exposure unit) 20 supported on the second support post 18 for vertical movement along its vertical axis, a vibration isolation mechanism (vibration suppressing mechanism) 22 (see FIG. 2) for suppressing or dampening vibration transmitted from the vehicle 12 to the main unit 20 and for connecting the first support post 16 to the second support post 18, and a fixing mechanism 23 for fixing the main unit 20 to the vehicle 12 when an image of a subject 40 (see FIG. 3) is captured by the main unit 20. The main unit 20 and the second support post 18 which supports the main unit 20 function as a holder.

The first support post 16 has a substantially rectangular horizontal cross section and includes a plate-like support base 24 disposed on the lower end thereof and lying substantially perpendicularly to the axis of the first support post 16. The support base 24 is fastened to the floor 14 in the compartment of the vehicle 12 by mounting bolts 26 (see FIG. 1).

A fixing bracket 30 is mounted on the upper end of the first support post 16 in facing relation to a wall 28 of the vehicle 12 which extends substantially perpendicularly to the floor 14. The first support post 16 is secured to the wall 28 by the fixing bracket 30 which is fastened to the wall 28 by mounting bolts 26. Therefore, the first support post 16 is firmly mounted in the compartment of the vehicle 12 by two members, i.e., the support base 24 and the fixing bracket 30.

As shown in FIG. 2, a box-shaped joint casing 32 is mounted on the upper end of the first support post 16. The fixing mechanism 23 includes a second lock 102 (described later on) mounted on a side wall of the joint casing 32, and the vibration isolation mechanism 22 is mounted on an upper wall of the joint casing 32.

The second support post 18 also has a substantially rectangular horizontal cross section. A storage casing 34 having a substantially channel-shaped cross section which is open toward the first support post 16 is provided on the lower end of the second support post 18 (see FIG. 2). The storage casing 34 stores therein the joint casing 32 mounted on the upper end of the first support post 16 and the vibration isolation mechanism 22. As shown in FIG. 2, the joint casing 32 has opposite side walls covered with respective side walls of the storage casing 34 which extend downwardly over the joint casing 32.

As shown in FIG. 1, a display unit 36 and a console panel 38 are mounted on the upper end of the second support post 18. The display unit 36 has a function to display instructions to be read by a patient as a subject 40 (see FIG. 3) for capturing an image of the subject 40. The console panel 38 is operated by the operator to activate the image forming apparatus 10, and has a function to display patient information, an exposure size, selectable items, and utility control information.

Figure 3:
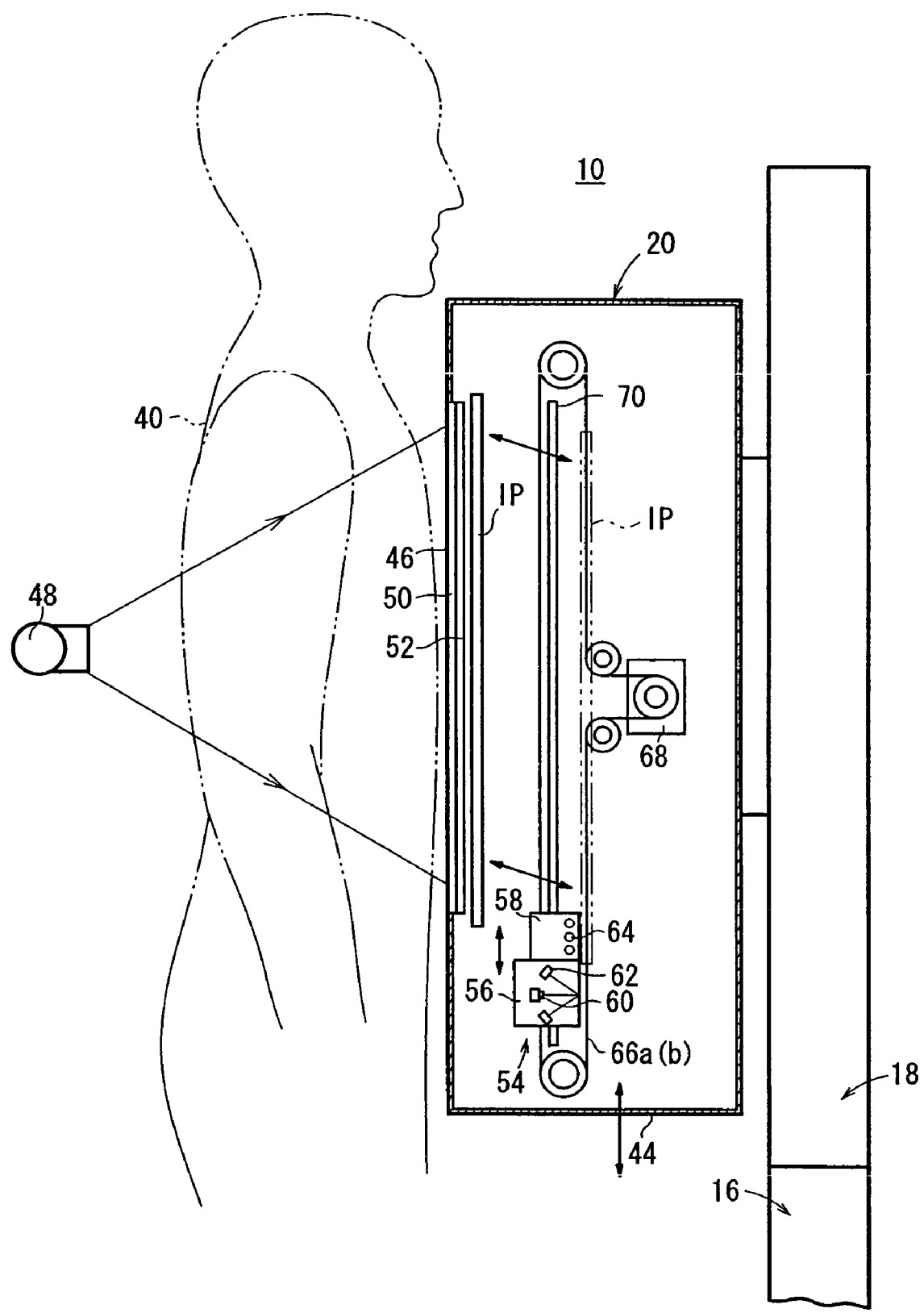
FIG. 3 is a fragmentary vertical cross-sectional view of a main unit and other components of the image forming apparatus shown in FIG. 1.

The main unit 20 has a pair of grip bars 42a, 42b (see FIG. 2) mounted on its opposite sides for the subject 40 (see FIG. 3) to grip to keep its posture for capturing its image. As shown in FIG. 3, the main unit 20 has a box-shaped housing 44 including a front panel serving as an exposure base 46 for positioning the subject 40 thereon. The exposure base 46 is combined with a phototimer 50 for measuring a dose of X-rays applied from a radiation source 48 through the subject 40 to control the amount of radiation to be applied, and a grid 52 for removing scattered rays.

The main unit 20 accommodates therein a stimulable phosphor sheet image panel ("IPD") that is movable between a position (indicated by the solid lines) close to the grid 52 and a position (indicated by the two-dot-and-dash lines) remote from the grid 52.

The main unit 20 also houses therein a reading/erasing unit 54 that is vertically movable along the front surface of the stimulable phosphor sheet IP which is in the position indicated by the two-dot-and-dash lines. The reading/erasing unit 54 comprises a reader 56 for applying stimulating light to the stimulable phosphor sheet IP and photoelectrically reading photostimulated luminescence emitted from the stimulable phosphor sheet IP depending on the intensity of radiation energy stored in the stimulable phosphor sheet IP as representing radiation image information, and an eraser 58 for applying erasing light to the stimulable phosphor sheet IP from which the radiation image information has been read to remove any remaining radiation energy from the stimulable phosphor sheet IP.

The reader 56 comprises a plurality of light sources 60 each having a laser diode for emitting stimulating light, and a plurality of charge-coupled device ("CCDD") line sensors 62 for converting the photostimulated luminescence emitted from the stimulable phosphor sheet IP into an electrical signal. The eraser 58 comprises a plurality of light sources 64 for emitting erasing light.

The reading/erasing unit 54 is connected to feed belts 66$a$, 66$b$ which are driven by a reading/erasing unit moving motor 68 to move the reading/erasing unit 54 vertically along guide rails 70 which extend vertically on both sides of the stimulable phosphor sheet IP.

As shown in FIG. 1, a controller 72 for controlling the image forming apparatus 10 is disposed outside of the main unit 20. The controller 72 is connected to the main unit 20 by a cable 74.

Figure 4:
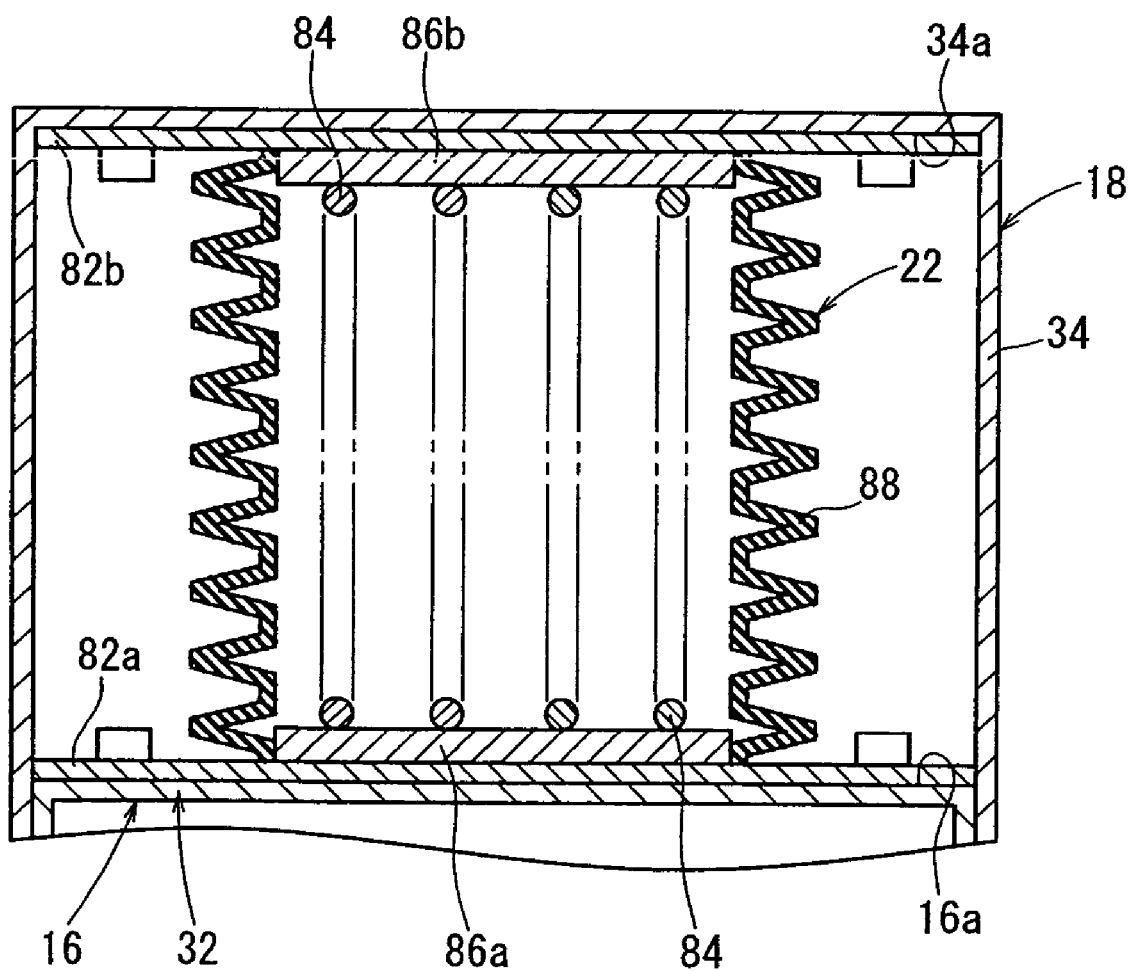
FIG. 4 is an enlarged vertical cross-sectional view of a vibration isolation mechanism shown in FIG. 2.

As shown in FIG. 4, the vibration isolation mechanism 22 comprises a first joint plate 82$a$ fixed to an upper end surface 16$a$ of the joint casing 32 on the first support post 16, a second joint plate 82$b$ fixed to an inner wall surface 34$a$ of the storage casing 34 on the second support post 18 which is spaced upwardly from and faces the upper end surface 16$a$ of the joint casing 32, a spring (resilient member) 84 such as helical springs, for example, interposed between the first and second joint plates 82$a$, 82$b$, and a cylindrical cover member 88 interposed between retainers 86$a$, 86$b$ mounted respectively on the first and second joint plates 82$a$, 82$b$ in covering relation to the spring 84.

The spring 84 comprises a plurality of equally spaced springs (resilient components) interconnecting the first and second joint plates 82$a$, 82$b$. The spring 84 has optimum characteristics, e.g., spring characteristics, material characteristics, etc., depending on the weights and the positions of the center of gravity of the second support post 18 and the main unit 20 which are supported by the vibration isolation mechanism 22, or various conditions such as vibrating conditions of the vehicle 12 while the vehicle 12 is being driven.

The second support post 18 and the main unit 20 which are supported on and above the vibration isolation mechanism 22 are held by the spring 84 of the vibration isolation mechanism 22 for three-dimensional swinging movement by predetermined distances along X-, Y-, and Z-axes with respect to the first support post 16.

Instead of the spring 84, a resilient body such as of rubber or the like, which may comprise a plurality of resilient members, may be interposed between the first and second joint plates 82$a$, 82$b$ and disposed in the cover member 88. Both such a resilient body and the spring 84 may be interposed between the first and second joint plates 82$a$, 82$b$ and disposed in the cover member 88. Stated otherwise, the vibration isolation mechanism 22 may have any means for damping vibration transmitted from the vehicle 12 through the first support post 16 to the second support post 18 and hence to the main unit 20.

The number of springs of the spring 84 and/or the number of resilient members of the resilient body is not limited to any particular value. The spring 84 may comprise a single spring or a plurality of springs, and the resilient body may comprise a single resilient member or a plurality of resilient members depending on the weights and the positions of the center of gravity of the second support post 18 and the main unit 20, or various conditions such as vibrating conditions of the vehicle 12 while the vehicle 12 is being driven.

If a resilient body is disposed in the cover member 88, then the cover member 88 may have optimum characteristics (e.g., material characteristics) selected depending on the weights and the positions of the center of gravity of the second support post 18 and the main unit 20 that are held by the vibration isolation mechanism 22, or various conditions such as vibrating conditions of the vehicle 12 while the vehicle 12 is being driven.

As shown in FIGS. 1 and 2, the fixing mechanism 23 comprises a first lock 100 mounted on the upper end of the second support post 18 for fixing the main unit 20 to the wall 28 of the vehicle 12 through the second support post 18, and a second lock 102 mounted in the joint casing 32 on the first support post 16 for securing the first support post 16 and the second support post 18 integrally to each other.

Figure 5:
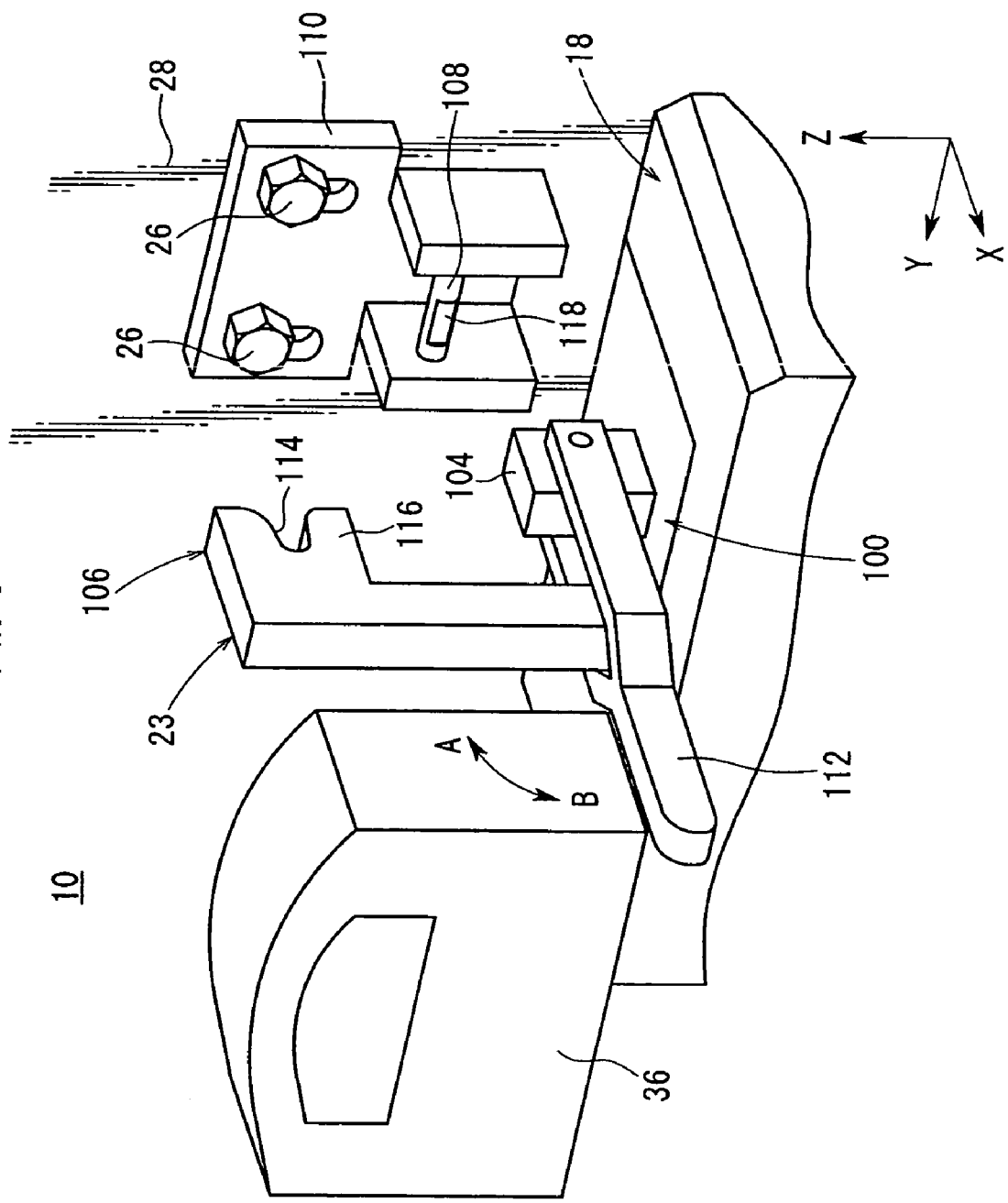
FIG. 5 is an enlarged fragmentary perspective view of a first lock of the fixing mechanism shown in FIG. 1 which is mounted on an upper end of a second support post.
Figure 6:
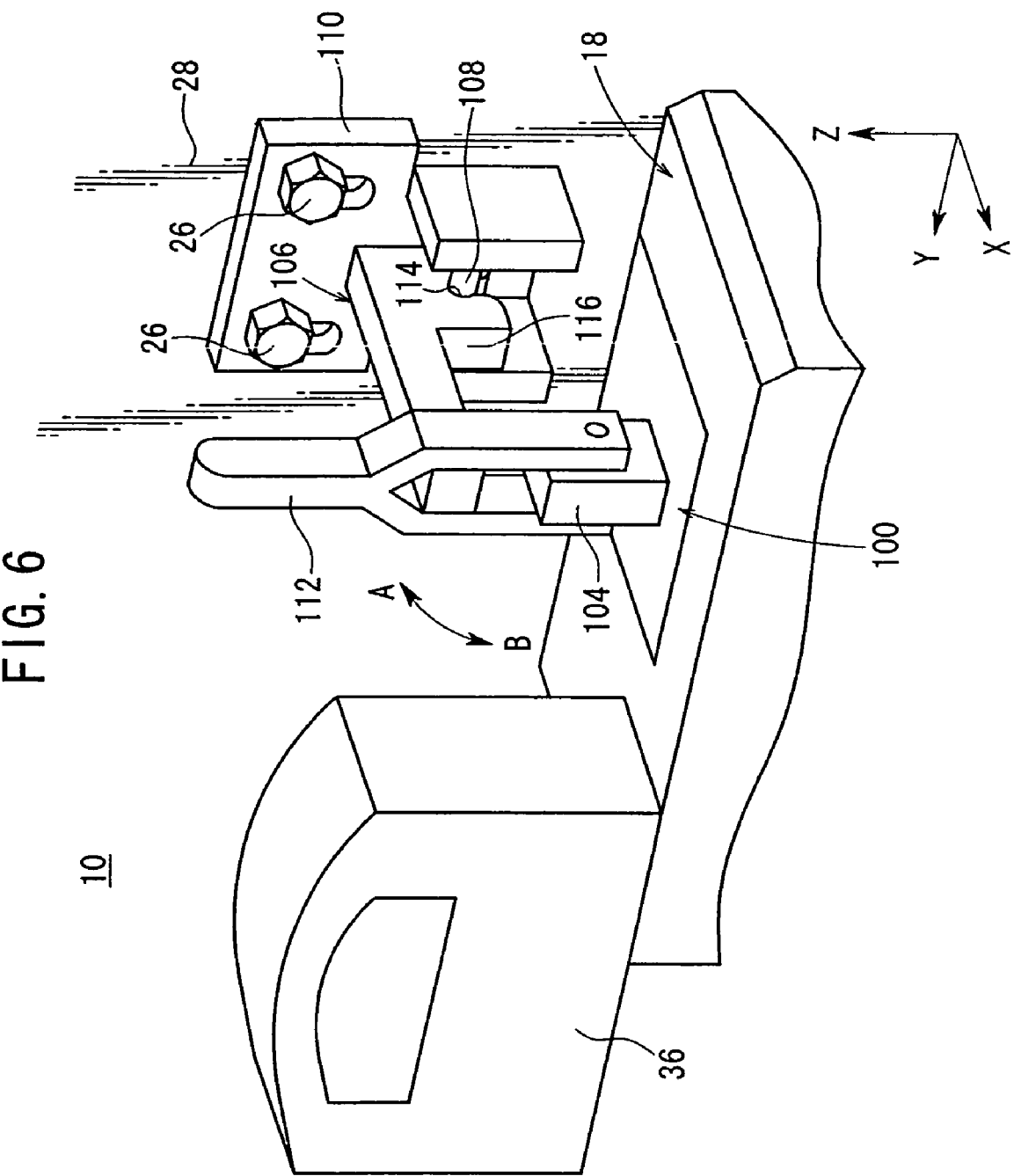
FIG. 6 is an enlarged fragmentary perspective view showing the manner in which the second support post is fixed to the wall surface of the vehicle by the first lock shown in FIG. 5.

As shown in FIGS. 5 and 6, the first lock 100 comprises a support member 104 mounted on the upper end surface of the second support post 18, and a lock arm 106 angularly movably supported on the support member 104. A bracket 110 having a substantially horizontal pin 108 is mounted by mounting bolts 26 to the wall 28 of the vehicle 12 which faces the first lock 100.

The lock arm 106 comprises a grip lever 112 which can be gripped and turned about the support member 104 by the operator and a clamp 116 extending substantially perpendicularly to the grip lever 112, the clamp 116 having an engaging slot 114 of a substantially U-shaped cross section. The engaging slot 114 is open toward the bracket 110. The clamp 116 is joined to an intermediate portion of the lock arm 106, which has a grip end and an opposite end that is pivotally supported on the support member 104.

The lock arm 106 operates as follows: If the grip lever 112 is turned toward the wall 28 of the vehicle 12 in the direction indicated by the arrow A, then the turning movement of the grip lever 112 is limited when the grip lever 112 extends vertically, i.e., substantially perpendicularly to the upper end surface of the second support post 18 (see FIG. 6). Conversely, if the grip lever 112 is turned away from the wall 28 of the vehicle 12, i.e., toward the display unit 36, in the direction indicated by the arrow B, then the turning movement of the grip lever 112 is limited when the grip lever 112 extends substantially horizontally, i.e., parallel to the upper end surface of the second support post 18 (see FIG. 5). Stated otherwise, the lock arm 106 is angularly movable through 90° with respect to the support member 104.

When the grip lever 112 is turned toward the wall 28 of the vehicle 12 in the direction indicated by the arrow A, the clamp 116 is turned toward the bracket 110 on the wall 28, causing the engaging slot 114 in the clamp 116 to fit over the pin 108 of the bracket 110. The second support post 18 and the main unit 20 are now prevented from being displaced toward and away from the wall 28 in the directions of the X-axis by the lock arm 106 of the first lock 100 (see FIG. 6).

As shown in FIG. 5, the pin 108 has a recess 118 defined centrally therein in its front side and extending in the axial direction of the pin 108 over a predetermined distance substantially equal to the width of the clamp 116. When the engaging slot 114 in the clamp 116 fits over the pin 108, the clamp 116 is engaged by the opposite ends of the recess 118, preventing the second support post 18 and the main unit 20 from being displaced substantially parallel to the wall 28 in the directions of the Y-axis (see FIG. 6). Accordingly, the second support post 18 and the main unit 20 are firmly secured to the wall 28 by the first lock 100 and the bracket 110.

When the grip lever 112 is turned away from the wall 28 of the vehicle 12 in the direction indicated by the arrow B, the clamp 116 is turned away from the pin 108 in the direction indicated by the arrow B. Since the clamp 116 is released from the first lock 100, the second support post 18 and the main unit 20 are disconnected from the wall 28 (see FIG. 5).

Figure 7:
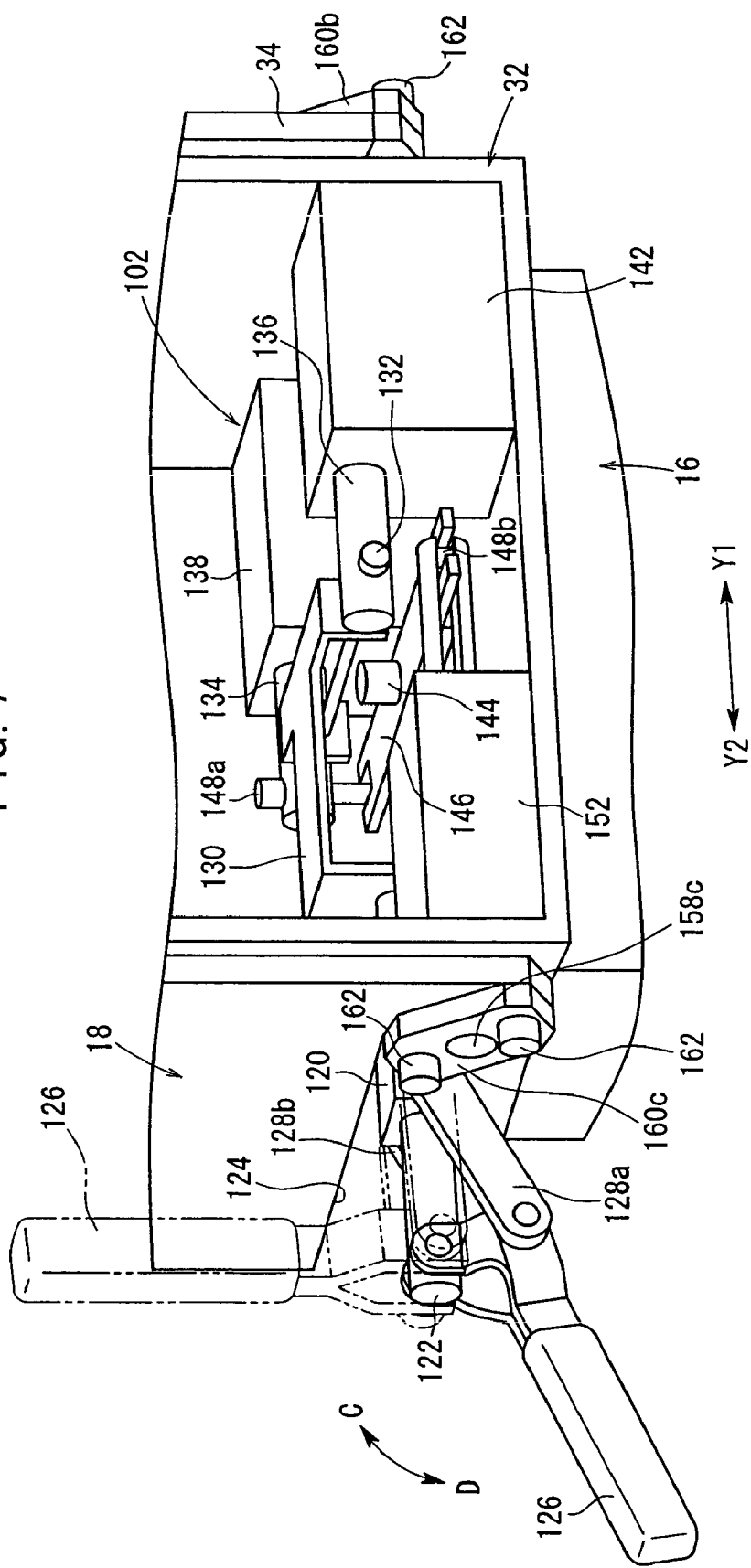
FIG. 7 is an enlarged fragmentary perspective view of a second lock of the fixing mechanism shown in FIG. 2.

As shown in FIG. 7, the second lock 102 has a shaft 122 extending through a guide block 120 fixedly mounted in the joint casing 32 (see also FIGS. 10 and 11) and guided thereby for displacement in its axial directions along the Y-axis. The shaft 122 extends substantially parallel to the main unit 20 and has an end projecting out of the joint casing 32 through an opening 124 that is defined in side walls of the joint casing 32 and the storage casing 34.

The second lock 102 also has a grip lever 126 attached to an end of the shaft 122. The grip lever 126 can be gripped by the operator to selectively lock the second support post 18 to the first support post 16 and unlock the second support post 18 from the first support post 16. The grip lever 126 is angularly movable about 90° about the end of the shaft 122 upwardly from a substantially horizontal position.

A pair of holder arms 128a, 128b has respective ends pivotally supported on the grip lever 126 at a position that is spaced a predetermined distance from the portion of the grip lever 126 that is pivotally supported on the shaft 122. The holder arms 128a, 128b have other ends pivotally supported on respective opposite sides of the guide block 120. When the grip lever 126 is turned upwardly in the direction indicated by the arrow C toward the joint casing 32, the grip lever 126 and the holder arms 128a, 128b are turned from the solid-line position to the two-dot-and-dash-line position shown in FIG. 7. The shaft 122 that is pivotally connected to the grip lever 126 is pushed into the joint casing 32, i.e., displaced in the direction indicated by the arrow Y1.

Conversely, when the grip lever 126 is turned in the direction indicated by the arrow D away from the joint casing 32, the grip lever 126 and the holder arms 128a, 128b are turned from the two-dot-and-dash-line position to the solid-line position, pulling the shaft 122 out of the joint casing 32, i.e., displacing the shaft 122 in the direction indicated by the arrow Y2.

That is, when the grip lever 126 that is limited against free angular movement by the holder arms 128a, 128b is turned in the directions indicated by the arrows C, D, the shaft 122 inserted in the guide block 120 can be displaced axially in the directions indicated by the arrows Y1, Y2.

Figure 10:
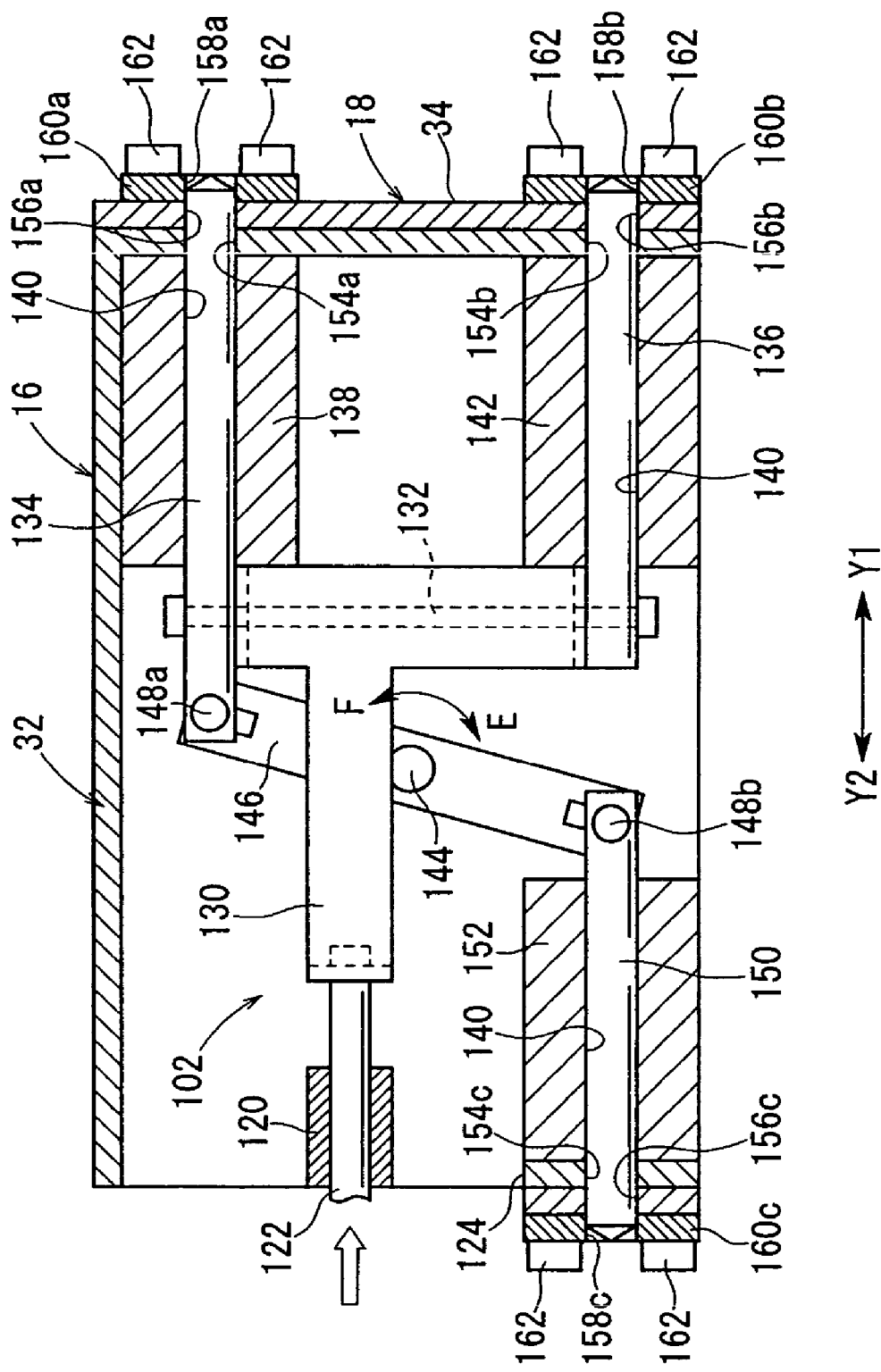
FIG. 10 is a horizontal cross-sectional view showing the manner in which first through third lock pins of the second lock shown in FIG. 7 extend through walls of a joint casing and the storage casing, joining the first support post to a second support post.
Figure 11:
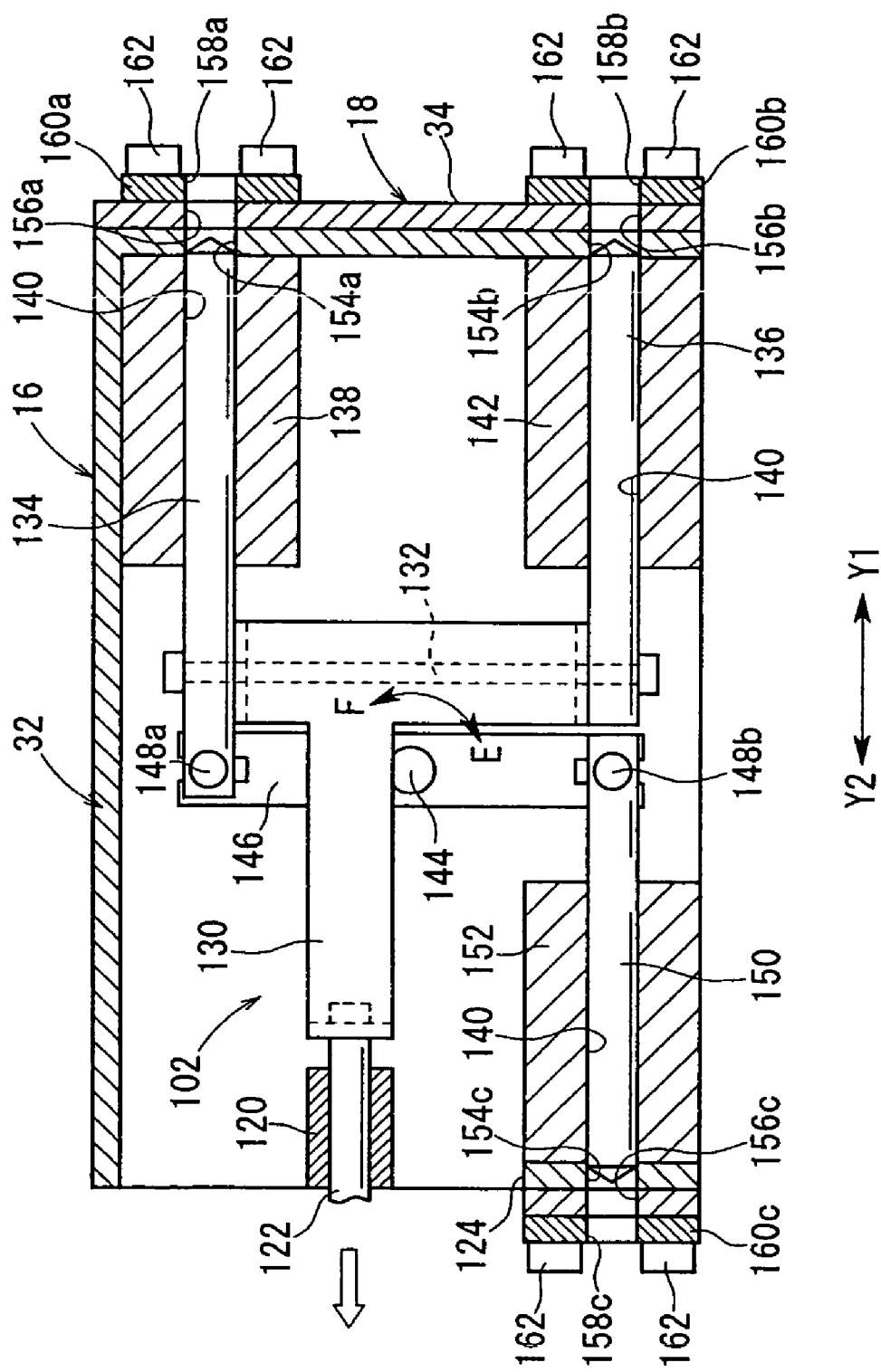
FIG. 11 is a horizontal cross-sectional view showing the manner in which the first through third lock pins of the second lock shown in FIG. 10 are retracted into the joint casing, releasing the first support post from the second support post.

As shown in FIGS. 7, 10, and 11, a substantially T-shaped connector 130 has an end joined to the other end of the shaft 122 which is located in the joint casing 32. The other end of the connector 130 has an arm extending perpendicularly to the axis thereof, and the arm has opposite ends supporting an elongate engaging pin 132 which extends through holes defined respectively in those opposite ends. The engaging pin 132 extends perpendicularly through ends of first and second lock pins 134, 136.

As shown in FIGS. 10 and 11, the first and second lock pins 134, 136 are spaced a predetermined distance from each other and extend substantially parallel to each other from the other end of the connector 130 away from the grip lever 126 in the direction indicated by the arrow Y1. The first and second lock pins 134, 136 lie substantially perpendicularly to the other end of the connector 130.

The first and second lock pins 134, 136 are of a cylindrical shape, and have substantially equal lengths along the axial directions thereof. The first lock pin 134 extends through a through hole 140 defined in a first holder block 138 which is held against one of the side walls of the joint casing 32 and disposed in the joint casing 32 closely to the main unit 20. The second lock pin 136 extends through a through hole 140 defined in a second holder block 142 which is held against the same side wall of the joint casing 32 substantially parallel to the first holder block 138 and disposed in the joint casing 32 remotely from to the main unit 20.

A support pin 144 is mounted substantially centrally in the joint casing 32 and extends substantially parallel to the axis of the first support post 16. A link arm 146 is angularly movably mounted on the support pin 144 for angular movement about the support pin 144. The link arm 146 has an end engaging a link pin 148a which is mounted on an end of the first lock pin 134 that is positioned out of the first holder block 138. The link arm 146 is pivotally supported on the first lock pin 134 at a position closer to the grip lever 126 than the position where the engaging pin 132 extends through the first lock pin 134.

The other end of the link arm 146 engages a link pin 148b mounted on an end of a third lock pin 150.

The link arm 146 is thus angularly movable about the support pin 144 when the first and third lock pins 134, 150 are axially displaced.

The third lock pin 150 is of a cylindrical shape and is disposed alongside of the guide block 120 in substantial alignment with the second lock pin 136. The third lock pin 150 extends through a through hole 140 defined in a third holder block 152 which is held against the other side wall of the joint casing 32 and disposed in the joint casing 32 remotely from the main unit 20.

The side wall of the joint casing 32 which is held against the first and second holder blocks 138, 142 has first holes 154a, 154b defined therein in alignment with the respective through holes 140 in the first and second holder blocks 138, 142.

The side wall of the joint casing 32 which is held against the third holder block 152 also has a first hole 154c defined therein in alignment with the through hole 140 in the third holder block 152.

The side walls of the storage casing 34 which face the respective side walls of the joint casing 32 have second holes 156a, 156b, 156c defined therein and having respective diameters substantially equal to those of the first holes 154a, 154b, 154c, respectively. The through holes 140 in the first, second, and third holder blocks 138, 142, 152 are held in communication with the first holes 154a, 154b, 154c, respectively, in the joint casing 32 and also with the second holes 156a, 156b, 156c, respectively, in the storage casing 34 (see FIGS. 10 and 11).

Figure 8:
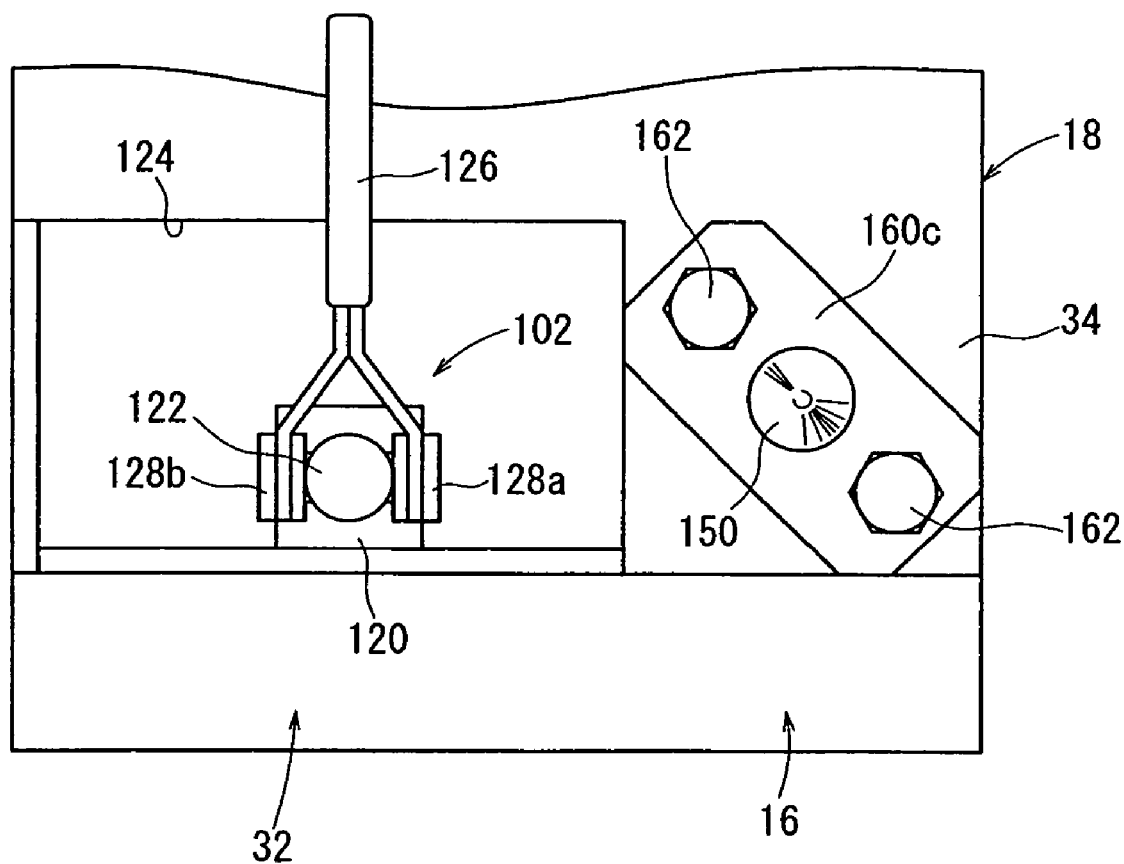
FIG. 8 is an enlarged right side elevational view of a storage casing of the second support post, as viewed from the right side of the image forming apparatus.
Figure 9:
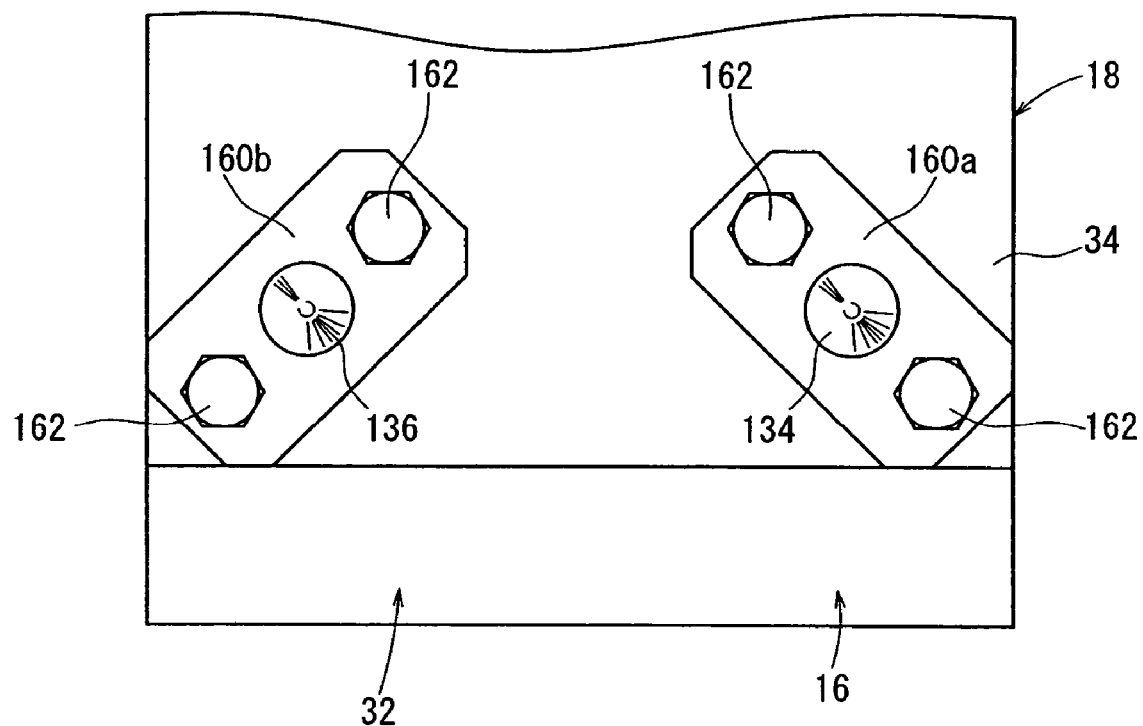
FIG. 9 is an enlarged left side elevational view of the storage casing of the second support post, as viewed from the left side of the image forming apparatus.

Guide plates 160a, 160b, 160c having respective guide holes 158a, 158b, 158c aligned with the second holes 156a, 156b, 156c, respectively, are mounted by bolts 162 on the opposite side walls of the storage casing 34 (see also FIGS. 8 and 9). The guide holes 158a, 158b, 158c have diameters substantially equal to those of the first, second, and third lock pins 134, 136, 150. When the first, second, and third lock pins 134, 136, 150 are inserted respectively into the guide holes 158a, 158b, 158c, the first, second, and third lock pins 134, 136, 150 are guided thereby for axial movement. The first, second, and third lock pins 134, 136, 150 that are inserted respectively into the guide holes 158a, 158b, 158c have tapered distal ends, respectively.

In the present embodiment, the second lock 102 selectively locks the second support post 18 and the main unit 20 to the vehicle 12 and unlocks the second support post 18 and the main unit 20 from the vehicle 12 when the grip lever 126 is manually turned. However, the first, second, and third holder blocks 138, 142, 152 may be replaced with solenoid-operated valves, and the solenoid-operated valves may be energized and de-energized to axially displace the first, second, and third lock pins 134, 136, 150 for electrically locking the second support post 18 and the main unit 20 to the vehicle 12 and unlocking the second support post 18 and the main unit 20 from the vehicle 12.

Figure 12:
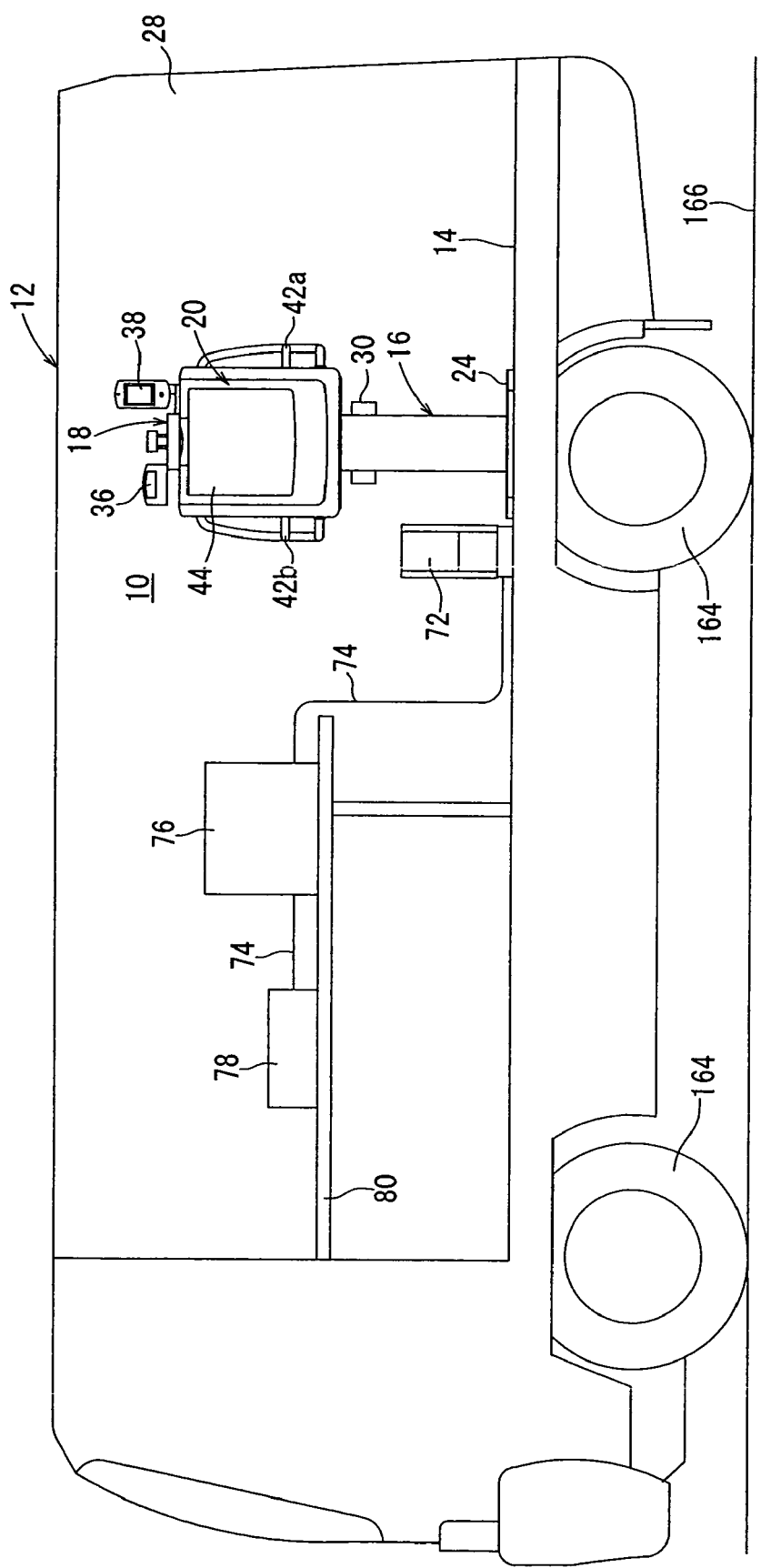
FIG. 12 is a schematic side elevational view showing a vehicle-mounted system including the image forming apparatus installed on the vehicle.

As shown in FIG. 12, a vehicle-mounted system which is installed in the compartment of the vehicle 12 includes an image processor 76 for confirming and processing image data and image information generated by the image forming apparatus 10, and a recorder 78 for saving image data and image information confirmed and processed by the image processor 76.

The image processor 76 is placed on the upper surface of a table 80 or the like and is connected to the controller 72 by a cable 74. The image processor 76 is also connected to the recorder 78 (e.g., a compact disc ("CDD") drive or a digital video disc ("DVDD") drive) by a cable 74. If a printer (not shown) is connected to the image processor 76, then the printer can print image data and image information confirmed and processed by the image processor 76.

After image data and image information have been confirmed and processed by the image processor 76, these image data and image information may be saved to a recording medium (not shown) such as a CD or a DVD by the recorder 78. Then, the recording medium with the stored image data and image information may be carried out of the vehicle 12.

The image forming apparatus 10 according to the present embodiment is basically constructed as described above. Operation and advantages of the image forming apparatus 10 will be described below.

First, operation of the vibration isolation mechanism 22 to suppress vibrations transmitted from the vehicle 12 to the main unit 20 of the image forming apparatus 10 will be described below. In this case, the first and second locks 100, 102 of the fixing mechanism 23 release the main unit 20 and the second support post 18 from the vehicle 12 and the first support post 16 (see FIGS. 1 and 2).

As shown in FIG. 12, while the vehicle 12 is being driven, vibrations from wheels 164 of the vehicle 12 are transmitted to the floor 14 and the wall 28 of the vehicle 12 and then to the first support post 16 that is fixed to the floor 14 and the wall 28.

The vibrations transmitted to the first post 16 are applied to the vibration isolation mechanism 22 connected to the upper end of the first support post 16, and dampened to a predetermined level by the springs of the spring 84 of the vibration isolation mechanism 22. The characteristics and the number of the springs of the spring 84 are established depending on the weights and the positions of the center of gravity of the second support post 18 and the main unit 20 which are swingably supported on the vibration isolation mechanism 22, or various conditions such as vibrating conditions of the vehicle 12 while the vehicle 12 is being driven. Consequently, the vibrations transmitted through the spring 84 are appropriately suppressed to a level small enough not to adversely affect the optical system in the main unit 20 that is supported on the second support post 18.

As a result, the vibrations from the vehicle 12 are essentially prevented from being transmitted to the second support post 18 that is joined to the first support post 16 by the vibration isolation mechanism 22, and hence to the main unit 20 supported on the second support post 18. Stated otherwise, when the vibrations from the vehicle 12 are transmitted through the first support post 16 to the vibration isolation mechanism 22, the vibrations are absorbed by the vibration isolation mechanism 22 and will not be applied directly to the second support post 18 and the main unit 20.

When the vehicle 12 is brought to a stop for capturing a radiation image of the subject 40 with the main unit 20 of the image forming apparatus 10, the main unit 20 which is swingably supported on the second support post 18 by the vibration isolation mechanism 22 needs to be securely joined to the vehicle 12 and the first support post 16 for protection against undesirable swinging displacement.

Operation of the fixing mechanism 23 to fix the second support post 18 which supports the main unit 20 thereon to the vehicle 12 and the first support post 16 will be described below.

As shown in FIG. 5, the grip lever 112 of the lock arm 106 is gripped and turned toward the wall 28 of the vehicle 12 in the direction indicated by the arrow A. The clamp 116 is turned toward the bracket 110 on the wall 28, and causes the engaging slot 114 to fit over the pin 108 of the bracket 110. The second support post 18 and the main unit 20 are now prevented from being displaced toward and away from the wall 28 in the directions of the X-axis by the lock arm 106 of the first lock 100 (see FIG. 6).

At the same time, since the clamp 116 is engaged by the opposite ends of the recess 118 defined substantially centrally in the pin 108, the second support post 18 and the main unit 20 are also prevented from being displaced substantially parallel to the wall 28 in the directions of the Y-axis. Thus, the second support post 18 on which the main unit 20 is supported is secured to the wall 28 by the first lock 100 against substantially horizontal displacement in the directions along the X- and Y-axes.

For securing the second support post 18 to the first support post 16 with the second lock 102 in the joint casing 32, as shown in FIG. 7, the grip lever 126 projecting from the joint casing 32 is gripped and turned upwardly from a substantially horizontal position toward the joint casing 32 in the direction indicated by the arrow C until the grip lever 126 lies substantially parallel to the confronting side wall of the joint casing 32 as indicated by the two-dot-and-dash lines in FIG. 7 (see FIG. 8).

As shown in FIG. 10, the shaft 122 pivotally coupled to the grip lever 126 is axially pushed into the joint casing 32 and displaced a predetermined distance along the direction indicated by the arrow Y1. The connector 130 coupled to the shaft 122 is displaced in the direction indicated by the arrow Y1, displacing the first and second lock pins 134, 136 axially in and along the through holes 140 in the first and second holder blocks 138, 142. As a result, the first and second lock pins 134, 136 are inserted through the first holes 154a, 154b of the joint casing 32 and the second holes 156a, 156b of the storage casing 34 into the respective guide holes 158a, 158b of the guide plates 160a, 160b. Since the first and second lock pins 134, 136 have the tapered distal ends, respectively, they can smoothly be inserted into the guide holes 158a, 158b.

At the same time, the displacement of the first lock pin 134 in the direction indicated by the arrow Y1 causes the end of the link arm 146 which is engaged by the first lock pin 134 to turn about the support pin 144 clockwise in the direction indicated by the arrow E (FIG. 10) away from the grip lever 126, and also causes the other end of the link arm 146 to turn about the support pin 144 clockwise in the direction indicated by the arrow E toward the third holder block 152.

The third lock pin 150 which engages the other end of the link arm 146 through the link pin 148b is pushed in the direction indicated by the arrow Y2 while being held by the third holder block 152. Therefore, the third lock pin 150 is axially displaced in and along the through hole 140 in the third holder block 152, and is inserted through the first hole 154c of the joint casing 32 and the second hole 156c of the storage casing 34 into the guide hole 158c of the guide plate 160c. Since the third lock pin 150 has the tapered distal end, it can smoothly be inserted into the guide hole 158c.

Inasmuch the first, second, and third lock pins 134, 136, 150 are inserted respectively into the guide holes 158a, 158b, 158c of the guide plates 160a, 160b, 160c through the first holes 154a, 154b, 154c and the second holes 156a, 156b, 156c, the joint casing 32 coupled to the first support post 16 and the storage casing 34 on the lower end of the second support post 18 are prevented from being displaced relatively to each other by the first, second, and third lock pins 134, 136, 150.

Specifically, since the first, second, and third lock pins 134, 136, 150 are inserted in the guide holes 158a, 158b, 158c which have respective diameters substantially equal to the outside diameters of the first, second, and third lock pins 134, 136, 150, the second support post 18 on which the guide plates 160a, 160b, 160c are mounted is prevented from being displaced in its axial directions along the Z-axis, and also from being displaced toward and away from the wall 28 in the directions along the X-axis.

That is, because the first support post 16 is fixed to the floor 14 of the vehicle 12 by the support base 24 and also to the wall 28 by the bracket 110, the second support post 18 fixed to the first support post 16 by the joint casing 32 is fixed to the vehicle 12.

Consequently, the main unit 20 that is supported on the second support post 18 is prevented by the first lock 100 from being displaced toward and away from the wall 28 in the directions along the X-axis and also from being displaced substantially parallel to the wall 28 in the directions along the Y-axis, and is prevented by the second lock 102 from being displaced in the axial directions of the second support post 18 along the Z-axis and also from being displaced toward and away from the wall 28 in the directions along the X-axis. Therefore, the main unit 20 is firmly fixed reliably to the vehicle 12 in the three-dimensional directions along the X-axis, the Y-axis, and the Z-axis by the fixing mechanism 23 having the first and second locks 100, 102.

Stated otherwise, while the vehicle 12 is being driven, the main unit 20 that is swingably supported on the first support post 16 by the vibration isolation mechanism 22 is not swingably displaced as it is reliably secured to the vehicle 12 by the fixing mechanism 23.

In the illustrated embodiment, it has been described that the main unit 20 and the second support post 18 are fixed to the vehicle 12 and the first support post 16 successively by the first lock 100 and the second lock 102 in the order named. However, the main unit 20 and the second support post 18 may be fixed to the vehicle 12 and the first support post 16 successively by the second lock 102 and the first lock 100 in the order named.

Operation of the image forming apparatus 10 fixed to the vehicle 12 with the second support post 18 and the main unit 20 locked by the fixing mechanism 23 against swinging displacement will be described below.

First, a process of recording radiation image information on a stimulable phosphor sheet IP will be described below. The reading/erasing unit 54 is held in a standby position at the lower end of its vertical moving stroke shown in FIG. 3. The stimulable phosphor sheet IP is positioned in the solid-line position close to the exposure base 46.

The operator operates the console panel 38 (see FIG. 1) on the second support post 18 and a control means (not shown) to move the main unit 20 vertically along the second post 18 to a position depending on the region of the subject 40 which is to be exposed. Then, the operator energizes the radiation source 48 to apply X-rays to the subject 40. The X-rays pass through the subject 40 and are applied through the phototimer 50 and the grid 52 to the stimulable phosphor sheet IP, recording radiation image information of the subject 40 on the stimulable phosphor sheet IP.

After the radiation image information is recorded on the stimulable phosphor sheet IP, the stimulable phosphor sheet IP is displaced from the solid-line position to the two-dot-and-dash-line position by a stimulable phosphor sheet moving motor (not shown). Then, the reading/erasing unit moving motor 68 is energized to cause the feed belts 66a, 66b to lift the reading/erasing unit 54, whereupon the reader 56 starts reading the radiation image information recorded on the stimulable phosphor sheet IP.

Specifically, the light sources 60 of the reader 56 emit stimulating light that is applied as a line of light to the stimulable phosphor sheet IP, as shown in FIG. 3. Upon exposure to the stimulating light, the stimulable phosphor sheet IP emits photostimulated luminescence commensurate with the radiation energy stored in the stimulable phosphor sheet IP. The emitted photostimulated luminescence is then converted by the CCD line sensors 62 that are positioned in a staggered array into an electrical signal, which is processed and transmitted to the image processor 76. At this time, the reader 56 moves upwardly along the guide rails 70 to scan the stimulable phosphor sheet IP for thereby two-dimensionally reading the radiation image information that is recorded on the stimulable phosphor sheet IP over its entire area.

The reading/erasing unit 54 moves up to the upper end of its stroke, whereupon the reader 56 completes the reading of the radiation image information from the stimulable phosphor sheet IP. Thereafter, the reading/erasing unit 54 starts move downwardly, and the eraser 58 performs an erasing process. Specifically, the eraser 58 applies erasing light emitted from the light sources 64 to the stimulable phosphor sheet IP while the reading/erasing unit 54 is descending. In response to the erasing light applied to the stimulable phosphor sheet IP, the stimulable phosphor sheet IP discharges remaining radiation energy. This process continues until the reading/erasing unit 54 reaches the lower end of its stroke, whereupon the erasing of remaining radiation energy from the entire area of the stimulable phosphor sheet IP is completed.

As shown in FIG. 12, the image processor 76 confirms and processes image data and image information acquired from the stimulable phosphor sheet IP through the controller 72 connected to the image forming apparatus 10. The image data and image information may be saved to a CD or a DVD by the recorder 78, or may be printed by a printer (not shown).

After the above image forming process performed by the image forming apparatus 10 is finished, if the vehicle 12 is to be driven again, then it is necessary to release the second support post 18 and the main unit 20 from the vehicle 12 through the fixing mechanism 23, and to make the main unit 20 supported on the second support post 18 swingable on the first support post 16 through the vibration isolation mechanism 22 to prevent undue vibrations from being transmitted from the vehicle 12 to the second support post 18 and the main unit 20.

First, the grip lever 112 of the lock arm 106 of the first lock 100 shown in FIG. 6 is gripped and turned away from the wall 28 of the vehicle 12 in the direction indicated by the arrow B. The lock arm 106 is disengaged from the pin 108 of the bracket 110, whereupon the first lock 100 is released from the wall 28.

Stated otherwise, the second support post 18 and the main unit 20 which have been prevented from being displaced by the first lock 100 is rendered displaceable in the substantially horizontal directions along the X- and Y-axes.

For releasing the second support shaft 18 from the first support post 16 with the second lock 102, as shown in FIG. 7, the grip lever 126 tilted upwardly of the end of the shaft 122 is turned away from the joint casing 32 in the direction indicated by the arrow D in FIG. 7 to a substantially horizontal position.

The shaft 122 pivotally coupled to the grip lever 126 is axially pulled out of the joint casing 32 and displaced a predetermined distance along the direction indicated by the arrow Y2.

At the same time, the displacement of the first lock pin 134 in the direction indicated by the arrow Y2 causes the end of the link arm 146 which is engaged by the first lock pin 134 to turn about the support pin 144 counterclockwise in the direction indicated by the arrow F (FIG. 10) toward the grip lever 126, and also causes the other end of the link arm 146 to turn about the support pin 144 counterclockwise in the direction indicated by the arrow F away from the third holder block 152. The link arm 146 is thus turned, the third lock pin 150 that is coupled thereto by the link pin 148*b* is pulled in the direction indicated by the arrow Y1.

When the connector 130 coupled to the shaft 122 is displaced from the position shown in FIG. 11 in the direction indicated by the arrow Y2, the first and second lock pins 134, 136 are displaced axially in and along the through holes 140 in the first and second holder blocks 138, 142. As a result, the distal ends of the first and second lock pins 134, 136 which have been inserted in the respective guide holes 158*a*, 158*b* of the guide plates 160*a*, 160*b* are displaced into the first holes 154*a*, 154*b*.

At the same time, the third lock pin 150 is axially displaced in and along the through hole 140 in the third holder block 152, and the distal end of the third lock pin 150 which has been inserted in the guide hole 158*c* of the guide plate 160*c* is displaced into the first hole 154*c*.

That is, the distal ends of the first, second, and third lock pins 134, 136, 150 which have been inserted in the guide holes 158*a*, 158*b*, 158*c* and the second holes 156*a*, 156*b*, 156*c* are inserted only in the respective first holes 154*a*, 154*b*, 154*c* upon displacement of the first, second, and third lock pins 134, 136, 150 into the joint casing 32. Therefore, the second support post 18 which has been prevented from being displaced with respect to the joint casing 32 by the first, second, and third lock pins 134, 136, 150 is now released from the joint casing 32.

Therefore, the main unit 20 that is supported on the second support post 18 is released from the locked state in which it has been prevented by the first lock 100 from being displaced toward and away from the wall 28 in the directions along the X-axis and also from being displaced substantially parallel to the wall 28 in the directions along the Y-axis, and is prevented from the locked state in which it has been prevented by the second lock 102 from being displaced in the axial directions of the second support post 18 along the Z-axis and also from being displaced toward and away from the wall 28 in the directions along the X-axis.

Consequently, the main unit 20 is rendered swingable in the three-dimensional directions along the X-axis, the Y-axis, and the Z-axis by the vibration isolation mechanism 22 which is disposed between the second support post 18 and the first support post 16.

In the illustrated embodiment, it has been described that the main unit 20 and the second support post 18 are released from the locked state successively by the first lock 100 and the second lock 102 in the order named. However, the main unit 20 and the second support post 18 may be released from the locked state successively by the second lock 102 and the first lock 100 in the order named.

For capturing an image of the subject 40 with the image forming apparatus 10, as described above, the second support post 18 and the main unit 20 are released from the vehicle 12. When the vehicle 12 with the image forming apparatus 10 installed thereon is driven, even if vibrations from the vehicle 12 are transmitted to the first support post 16, the vibrations are dampened by the springs of the spring 84 of the vibration isolation mechanism 22, and hence any vibrations transmitted from the first support post 16 to the second support post 18 are suppressed.

At this time, the level of vibrations dampened by the vibration isolation mechanism 22 and transmitted from the first support post 16 to the second support post 18 is reduced to a numerical value small enough not to adversely affect the optical system in the main unit 20. Therefore, undue vibrations generated when the vehicle 12 with the high resolution image forming apparatus 10 installed thereon is driven are prevented from being transmitted to the main unit 20. After the vehicle 12 with the image forming apparatus 10 installed thereon has traveled a certain distance, the image forming apparatus 10 is capable of taking pictures of the subject 40.

Specifically, while the vehicle 12 with the image forming apparatus 10 is being driven, the second support post 18 and the main unit 20 are released from the vehicle 12 and the first support post 16, so that the second support post 18 supporting the main unit 20 is allowed to be swingably displaced with respect to the first support post 16 and the vehicle 12. When the vehicle 12 is stopped to form an image with the image forming apparatus 10, the second support post 18 and the main unit 20 are fixed to the vehicle 12 and the first support post 16 by the fixing mechanism 23, so that the main unit 20 is prevented from being swingably displaced.

The image forming apparatus 10 according to the present embodiment employs a computed radiography ("CRD") system which uses the stimulable phosphor sheet IP in the main unit 20 for storing part of radiation energy and emitting photostimulated luminescence commensurate with the stored energy in response to stimulating light such as a laser beam, visible light, or the like. However, the present invention is not limited to the CR system, but may be applicable to a solid-state sensor system such as a Flat Panel Detector ("FPD") or the like capable of converting detected X-ray energy into an electrical signal for producing an image.

According to the present embodiment, as described above, the image forming apparatus 10 has the vibration isolation mechanism 22 for preventing vibrations produced when the vehicle 12 is driven from being transmitted to the main unit 20, disposed between the first support post 16 fixed to the floor 14 and the wall 28 in the compartment of the vehicle 12 and the second support post 18 which supports the main unit 20 for capturing an image of the subject 40.

After vibrations produced by the vehicle 12 while the vehicle 12 is being driven are transmitted to the first support post 16, the vibrations are dampened by the vibration isolation mechanism 22 which is mounted in the joint casing 32 on the first support post 16. Therefore, the vibrations are effectively prevented from being transmitted to the second support post 18 and the main unit 20.

Consequently, the main unit 20 which has the optical system susceptible to vibrations is reliably protected from vibrations while the vehicle 12 is being driven, and the image forming apparatus 10 that has the high-precision main unit 20 which has the optical system susceptible to vibrations can be installed on the vehicle 12.

In the image forming apparatus 10, the vibration isolation mechanism 22 is of a simple structure having a plurality of springs as the spring 84, and is housed between the joint casing 32 on the first support post 16 fixed to the vehicle 12 and the storage casing 34 on the second support post 18 that supports the main unit 20. Therefore, even though the image forming apparatus 10 incorporates the vibration isolation mechanism 22, the image forming apparatus 10 is not unduly large in size, and the limited space available in the compartment of the vehicle 12 can effectively be utilized for installation of the image forming apparatus 10 on the vehicle 12.

If various conditions with respect to vibrations to be dampened are changed, e.g., if the vehicle 12 for installing the image forming apparatus 10 is changed, if the conditions in which the vehicle 12 is driven are changed, or if the weight, etc. of the main unit 20 is changed, then the characteristics (e.g., spring characteristics) of the spring 84 are changed to optimum characteristics, and the number of springs of the spring 84 is also changed. Therefore, the vibration isolation mechanism 22 is capable of appropriately handling changes in the conditions with respect to vibrations to be dampened for effectively preventing vibrations from being transmitted from the vehicle 12 to the main unit 20.

The vibration isolation mechanism 22 for isolating vibrations can be manufactured at a relatively low cost as it is of a simple structure constructed by a plurality of springs as the spring 84.

After the vehicle 12 is driven and when it is stopped for the main unit 20 to capture an image of the subject 40, it is necessary to prevent the main unit 20 that is held by the vibration isolation mechanism 22 from being swingably displaced with respect to the first support post 16. To meet this requirement, the fixing mechanism 23 is provided for fixing the second support post 18 which supports the main unit 20 to the vehicle 12.

While the vehicle 12 is being driven, the vibration isolation mechanism 22 prevents vibrations from being transmitted from the vehicle 12 to the second support post 18 which supports the main unit 20. When the vehicle 12 is stopped to capture an image of the subject 40, the fixing mechanism 23 firmly secures the main unit 20 to the vehicle 12, so that the main unit 20 can capture a picture of the subject in an ordinary fashion.

Although a certain preferred embodiment of the present invention has been shown and described in detail, it should be understood that various changes and modifications may be made therein without departing from the scope of the appended claims.

What is claimed is:

1. A vibration isolation structure for an image-forming apparatus, comprising:

an exposure unit disposed in a compartment of a vehicle with wheels, for applying radiation to a subject and capturing a radiation image of the subject;

a support post fixedly mounted in the compartment of the vehicle;

a holder for holding the exposure unit; and a vibration-suppressing mechanism disposed between the support post and the holder for connecting the support post and the holder to each other to suppress vibrations generated while the vehicle is being driven and transmitted from the vehicle through the support post to the holder.

2. The vibration isolation structure of claim 1, wherein the vibration-suppressing mechanism comprises:

a resilient member disposed between the support post and the holder;

wherein the resilient member holds the holder swingably with respect to the support post.

3. The vibration isolation structure of claim 2, wherein the resilient member comprises:

an end engaging an upper surface of the support post; and an opposite end engaging a lower surface of the holder.

4. The vibration isolation structure of claim 2, wherein the resilient member comprises a helical spring.

5. The vibration isolation structure of claim 2, wherein the resilient member comprises a plurality of resilient components.

6. The vibration isolation structure of claim 2, wherein the resilient member has characteristics established depending on:

the weight and position of the center of gravity of the holder;

the weight and position of the center of gravity of the exposure unit; and conditions in which the vehicle is driven.

* * * * *